United States Patent
Westlund et al.

(10) Patent No.: US 8,290,584 B2
(45) Date of Patent: *Oct. 16, 2012

(54) METHOD AND APPARATUS FOR OPTIMIZING VAGAL NERVE STIMULATION USING LARYNGEAL ACTIVITY

(75) Inventors: Randy Westlund, River Falls, WI (US); Anthony V. Caparso, San Jose, CA (US); Mark Bly, Falcon Heights, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 115 days.

This patent is subject to a terminal disclaimer.

(21) Appl. No.: 12/872,408

(22) Filed: Aug. 31, 2010

(65) Prior Publication Data
US 2010/0324628 A1 Dec. 23, 2010

Related U.S. Application Data

(63) Continuation of application No. 11/469,551, filed on Sep. 1, 2006, now Pat. No. 7,801,603.

(51) Int. Cl.
*A61N 1/36* (2006.01)
(52) U.S. Cl. ............................................. 607/2; 607/46
(58) Field of Classification Search .............. 607/2, 20, 607/41, 46, 47, 118
See application file for complete search history.

(56) References Cited

U.S. PATENT DOCUMENTS

| | | | |
|---|---|---|---|
| 4,817,628 A | 4/1989 | Zealear et al. | |
| 5,111,814 A | 5/1992 | Goldfarb | |
| 5,263,491 A | 11/1993 | Thornton | |
| 5,275,159 A | 1/1994 | Griebel | |
| 5,590,241 A | 12/1996 | Park et al. | |
| 5,865,759 A | 2/1999 | Koblanski | |
| 6,721,603 B2 | 4/2004 | Zabara et al. | |
| 7,069,082 B2 | 6/2006 | Lindenthaler | |
| 7,801,601 B2* | 9/2010 | Maschino et al. | 607/2 |
| 7,801,603 B2* | 9/2010 | Westlund et al. | 607/2 |
| 2002/0169485 A1 | 11/2002 | Pless et al. | |
| 2003/0149457 A1 | 8/2003 | Tcheng et al. | |
| 2005/0010265 A1 | 1/2005 | Baru et al. | |
| 2005/0107843 A1 | 5/2005 | McDermott et al. | |
| 2008/0058874 A1 | 3/2008 | Westlund et al. | |
| 2008/0071318 A1* | 3/2008 | Brooke et al. | 607/28 |

FOREIGN PATENT DOCUMENTS
WO WO-2008030348 A1 3/2008

OTHER PUBLICATIONS

"U.S. Appl. No. 11/469,551, Examiner Interview Summary mailed Mar. 26, 2010", 3 pgs.
"U.S. Appl. No. 11/469,551, Non-Final Office Action mailed Dec. 21, 2009", 9 Pgs.

(Continued)

*Primary Examiner* — Brian T Gedeon
(74) *Attorney, Agent, or Firm* — Schwegman Lundberg & Woessner, P.A.

(57) ABSTRACT

A neural stimulation system delivers neural stimulation to the vagus nerve and senses a signal indicative of laryngeal activity resulting from the neural stimulation. The signal indicative of laryngeal activity is used, for example, to guide electrode placement, determine stimulation threshold, detect lead/electrode problems, detect neural injury, and monitor healing processing following the electrode placement inside the body of a patient.

20 Claims, 12 Drawing Sheets

OTHER PUBLICATIONS

"U.S. Appl. No. 11/469,551, Notice of Allowance mailed May 20, 2010", 7 pages.

"U.S. Appl. No. 11/469,551, Response filed Apr. 13, 2010 to Non Final Office Action mailed Dec. 21, 2009", 15 pgs.

"European Application Serial No. 07837286.9, Office Action mailed Sep. 29, 2009", 2 pgs.

"PCT Application No. PCT/US2007/018696, International Search Report mailed Jan. 21, 2008", 4 pgs.

"PCT Application No. PCT/US2007/018696, Written Opinion mailed Jan. 21, 2008", 7 pgs.

"Australian Application Serial No. 2007293449, First Examiner Report mailed Sep. 10, 2010", 1 pgs.

"European Application Serial No. 07837286.9, Response filed Jan. 7, 2010 to Office Action mailed Sep. 29, 2009", 14 pgs.

"Japanese Application Serial No. 2009-526650, Amended Claims filed Aug. 19, 2010", (w/ English Translation of Amended Claims), 12 pgs.

"Australian Application Serial No. 2007293449, Response filed Jun. 23, 2011 to First Examiner Report mailed Sep. 10, 2010", 18 pgs.

"Chinese Application Serial No. 200780040290.0, Office Action mailed Aug. 15, 2011", 14 pgs.

"Chinese Application Serial No. 200780040290.0, Response filed Nov. 23, 2011 to Office Action mailed Aug. 15, 2011", 12 pgs.

* cited by examiner

METHOD AND APPARATUS FOR OPTIMIZING VAGAL NERVE STIMULATION USING LARYNGEAL ACTIVITY

CLAIM OF PRIORITY

This application is a continuation of and claims the benefit of priority under 35 U.S.C. §120 to U.S. patent application Ser. No. 11/469,551, filed on Sep. 1, 2006, now issued as U.S. Pat. No. 7,801,603, which is hereby incorporated by reference herein in its entirety.

TECHNICAL FIELD

This document relates generally to neural stimulation and particularly to a system and method for optimizing vagal nerve stimulation using an activity sensor that senses a signal indicative of laryngeal activity.

BACKGROUND

Vagal nerve stimulation has been applied to modulate various physiologic functions and treat various diseases. One example is the modulation of cardiac functions in a patient suffering heart failure or myocardial infarction. The myocardium is innervated with sympathetic and parasympathetic nerves including the cardiac branches of the vagus nerve. Activities in the vagus nerve, including artificially applied electrical stimuli, modulate the heart rate and contractility (strength of the myocardial contractions). Electrical stimulation applied to the vagus nerve is known to decrease the heart rate and the contractility, lengthening the systolic phase of a cardiac cycle, and shortening the diastolic phase of the cardiac cycle. This ability of the vagal nerve stimulation is utilized, for example, to control myocardial remodeling.

In addition to treating cardiac disorders such as myocardial remodeling, vagal nerve stimulation is also know to be effective in treating disorders including, but not limited to, depression, anorexia nervosa/eating disorders, pancreatic function, epilepsy, hypertension, inflammatory disease, and diabetes. The intended therapy outcomes of vagal nerve stimulation in treating such disorders may be difficult to measure, either acutely or chronically, for purposes of therapy titration or optimization. Therefore, there is a need for titrating or optimizing vagal nerve stimulation using parameters other than the intended therapy outcomes.

SUMMARY

A neural stimulation system delivers neural stimulation to the vagus nerve and senses a signal indicative of laryngeal activity resulting from the neural stimulation. The signal indicative of laryngeal activity is used, for example, to guide electrode placement, determine stimulation threshold, detect lead/electrode problems, detect neural injury, and monitor healing processing following the electrode placement inside the body of a patient.

In one embodiment, a neural stimulation system includes an activity sensor and a neural stimulation analyzer. The activity sensor senses a signal indicative of laryngeal activity. The neural stimulation analyzer includes a laryngeal activity input to receive the signal indicative of laryngeal activity, a neural stimulation input to receive a signal indicative of the delivery of the neural stimulation to the vagus nerve, and a processing circuit. The processing circuit processes the signal indicative of laryngeal activity for analyzing the neural stimulation system using the signal indicative of laryngeal activity.

In one embodiment, a neural stimulation system includes an activity sensor, a signal conditioning circuit, a neural stimulation circuit, and a presentation device. The activity sensor senses a signal indicative of laryngeal activity. The signal conditioning circuit conditions the signal indicative of laryngeal activity. The neural stimulation circuit delivers neural stimulation to the vagus nerve. The presentation device presents indicators of the laryngeal activity and the delivery of the neural stimulation.

In one embodiment, a method for applying neural stimulation is provided. A signal indicative of laryngeal activity is sensed. The neural stimulation is delivered to the vagus nerve. The signal indicative of laryngeal activity is conditioned to isolate laryngeal activity resulting from the delivery of the neural stimulation.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
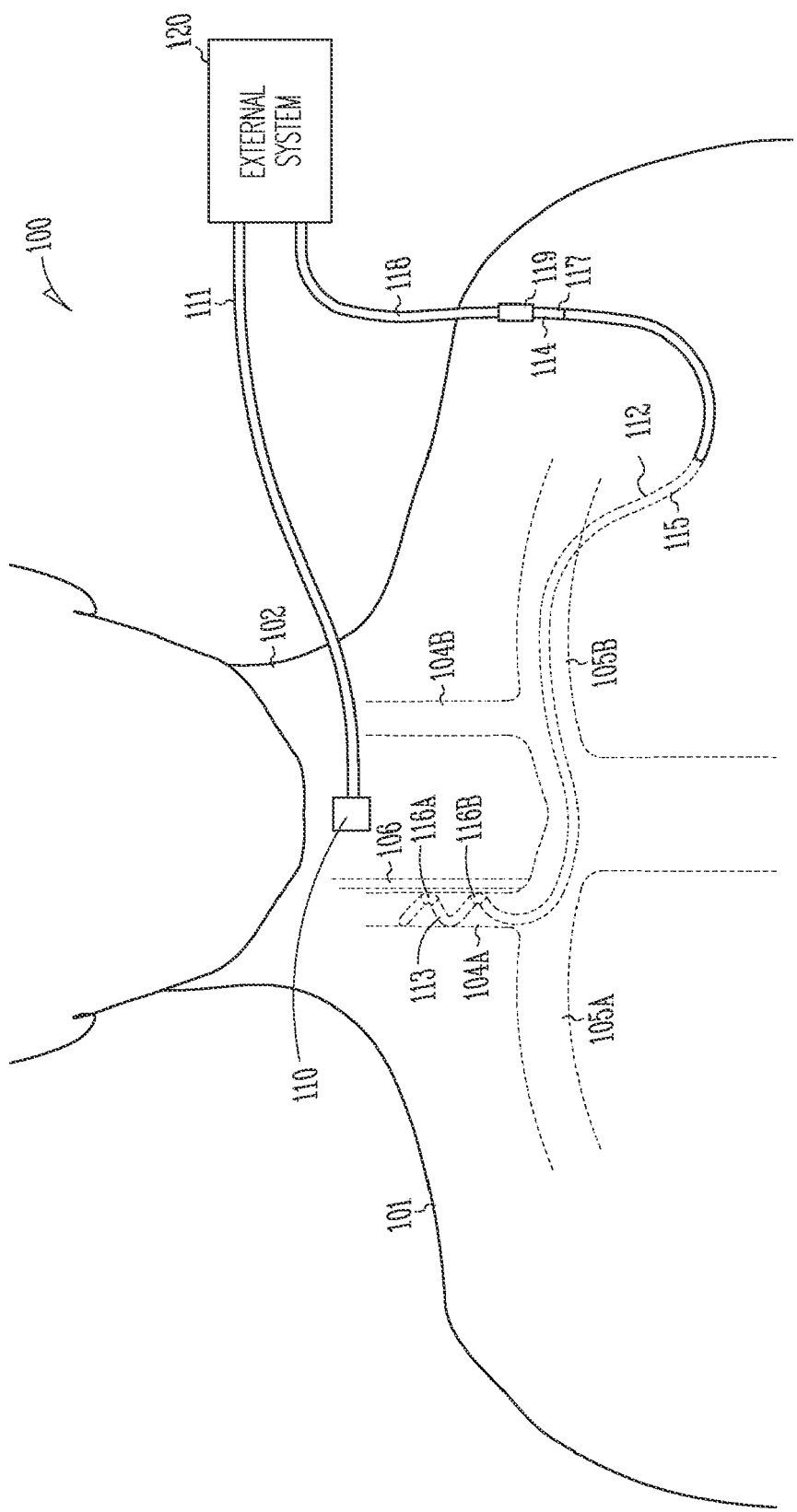
FIG. 1 is an illustration of an embodiment of a neural stimulation system and portions of an environment in which the neural stimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a system providing for optimization of vagal nerve stimulation using a laryngeal activity sensor. The optimization includes, for example, optimization of electrode placement, automatic threshold determination or verification, monitoring of lead/electrode status, detecting of neural injury, and monitoring a healing process that follows the electrode placement. In many applications of vagal nerve stimulation, the target response (intended outcome) may be difficult to monitor and analyze for the purpose of therapy optimization. For example, a transvenous lead is used to deliver vagal nerve stimulation for controlling cardiac remodeling. The transvenous lead includes one or more electrodes at its distal end to be placed within an internal jugular vein adjacent to the vagus nerve in the cervical region. The internal jugular vein is a large vessel providing for a wide range of possible electrode positions. It is practically difficult to use effects of the vagal nerve stimulation in cardiac remodeling for guidance in the electrode placement and stimulation parameter adjustment.

On the other hand, it is known that vagal nerve stimulation causes vibration of the larynx through the recurrent laryngeal nerves, which are branches of the vagus nerve that innervate the larynx. Thus, laryngeal activity, including the magnitude and frequency of the vibration of the larynx, provides for an indication of whether the vagus nerve is activated by neural stimulation. This allows for optimization of therapy without the need to monitor and analyze the target response (such as cardiac remodeling) of the vagal nerve stimulation.

The present subject matter is applicable to stimulation of the vagus nerve using various energy forms and various signal morphology. In one embodiment, vagal nerve stimulation includes delivery of electrical pulses to the vagus nerve to artificially elicit action potentials in that nerve. In other embodiments, vagal nerve stimulation includes delivery of any form of energy that is capable of eliciting or modulating neural activities in the nervous system, such as mechanical, thermal, optical, chemical, and biological energies.

The present subject matter is applicable to neural stimulation systems providing for activation and/or inhibition of the vagus nerve for treatment of various disorders including, but not limited to, cardiac remodeling, depression, anorexia nervosa/eating disorders, pancreatic function, epilepsy, hypertension, inflammatory disease, and diabetes. In general, the present subject matter is applicable to any system providing for vagal nerve stimulation in which the neural stimulation results in detectable laryngeal activity.

While delivery of neural stimulation through a transvenous lead having one or more electrodes placed in an internal jugular vein adjacent to the vagus nerve in the cervical region is specifically discussed in this document as an example, the present subject matter is applicable to any lead and/or electrode configuration and placement for vagal nerve stimulation. Optimization of electrode placement and stimulation parameters using laryngeal activity is particularly useful when the target response of the neural stimulation is difficult to measure acutely and/or when the intended stimulation site is difficult to locate precisely without a substantially invasive surgical procedure.

FIG. 1 is an illustration of an embodiment of a neural stimulation system 100 and portions of an environment in which system 100 is used. System 100 includes an activity sensor 110 for sensing laryngeal activity, a transvenous lead 112 for delivering vagal nerve stimulation, and an external system 120 coupled to activity sensor 110 via a cable 111 and coupled to lead 112 via a cable 118. External system 120 allows for optimization of the vagal nerve stimulation using the sensed laryngeal activity.

Lead 112 is a transvenous lead having a proximal end 114, a distal end 113, and an elongate body 115 coupled between proximal end 114 and distal end 113. Proximal end 114 includes a connector 117. In the illustrated embodiment, distal end 113 includes stimulation electrodes 116A-B. As illustrated in FIG. 1, a body 101 includes a neck 102, a right internal jugular vein 104A, a left internal jugular vein 104B, a right subclavian vein 105A, and a left subclavian vein 105B. Lead 112 is inserted using techniques similar to those employed in implanting cardiac pacing leads. During the insertion, distal end 113 enters the left subclavian vein 105B through an incision, advances in the subclavian veins 105B and then 105A toward right internal jugular vein 104A, enters right internal jugular vein 104A, advances in right internal jugular vein 104A until electrodes 116A-B reach one or more vagal nerve stimulation sites. After distal end 113 is in right internal jugular vein 104A, stimulation electrodes 116A-B are positioned, and repositioned when necessary, using lead 112 and/or a lead insertion tool such as a stylet, a guide wire, or a guide catheter.

Electrodes 116A-B allow neural stimulation to be delivered to a vagus nerve 106, which is adjacent to right internal jugular vein 104A in the cervical region. Activity sensor 110 is placed on the neck over the larynx to sense a signal indicative of laryngeal activity. The laryngeal activity is used as a measure of response of vagus nerve 106 to the neural stimulation delivered to vagus nerve 106. In various embodiments, the laryngeal activity is monitored for placement of stimulation electrodes such as electrodes 116A-B, optimization of stimulation parameter such as those controlling stimulation intensity (e.g., stimulation amplitude, frequency, duration, and duty cycle), and detection or monitoring of various events that affect the response of vagal nerve 106 to the neural stimulation.

As illustrated in FIG. 1, proximal end 114 remains outside of body 101, such as during an operation of implantation of lead 112 and an implantable medical device such as one discussed below with reference to FIG. 2. This allows electrodes 116A-B to be placed as desired before connecting proximal end 114 to the implantable medical device. Proximal end 114 includes a connector 117 coupled to a connector 119 of cable 118 to allow delivery of the neural stimulation from external system 120. External system 120 allows a user such as a physician or other caregiver to control the delivery of neural stimulation via lead 112 and monitor the signal indicative of larynx sensed by activity sensor 110.

The configuration of system 100 shown in FIG. 1 is an example presented for illustrative purposes. The present subject matter generally includes monitoring and optimization of vagal nerve stimulation delivered using any electrode configuration using any signal that indicates laryngeal activity resulting from the vagal nerve stimulation. For example, lead 112 may include one or more stimulation electrodes, and an electrode pair for delivering the neural stimulation may include two electrodes on lead 112 or an electrode on lead 112 and a reference electrode not necessarily adjacent to the vagus nerve. In one embodiment, the reference electrode is a skin patch electrode for acute use. In one embodiment, in addition to, or instead of, stimulation electrodes on lead 112 one or more nerve cuff electrodes each surrounding vagus nerve 106 are used. In one embodiment, electrodes 116A-B are placed in the left interval jugular vein 104B. During the insertion, distal end 113 enters the left subclavian vein 105B or right subclavian vein 105A through an incision, enters left internal jugular vein 104B from right subclavian vein 105A, advances in left internal jugular vein 104B until electrodes 116A-B reach one or more vagal nerve stimulation sites.

Figure 2:
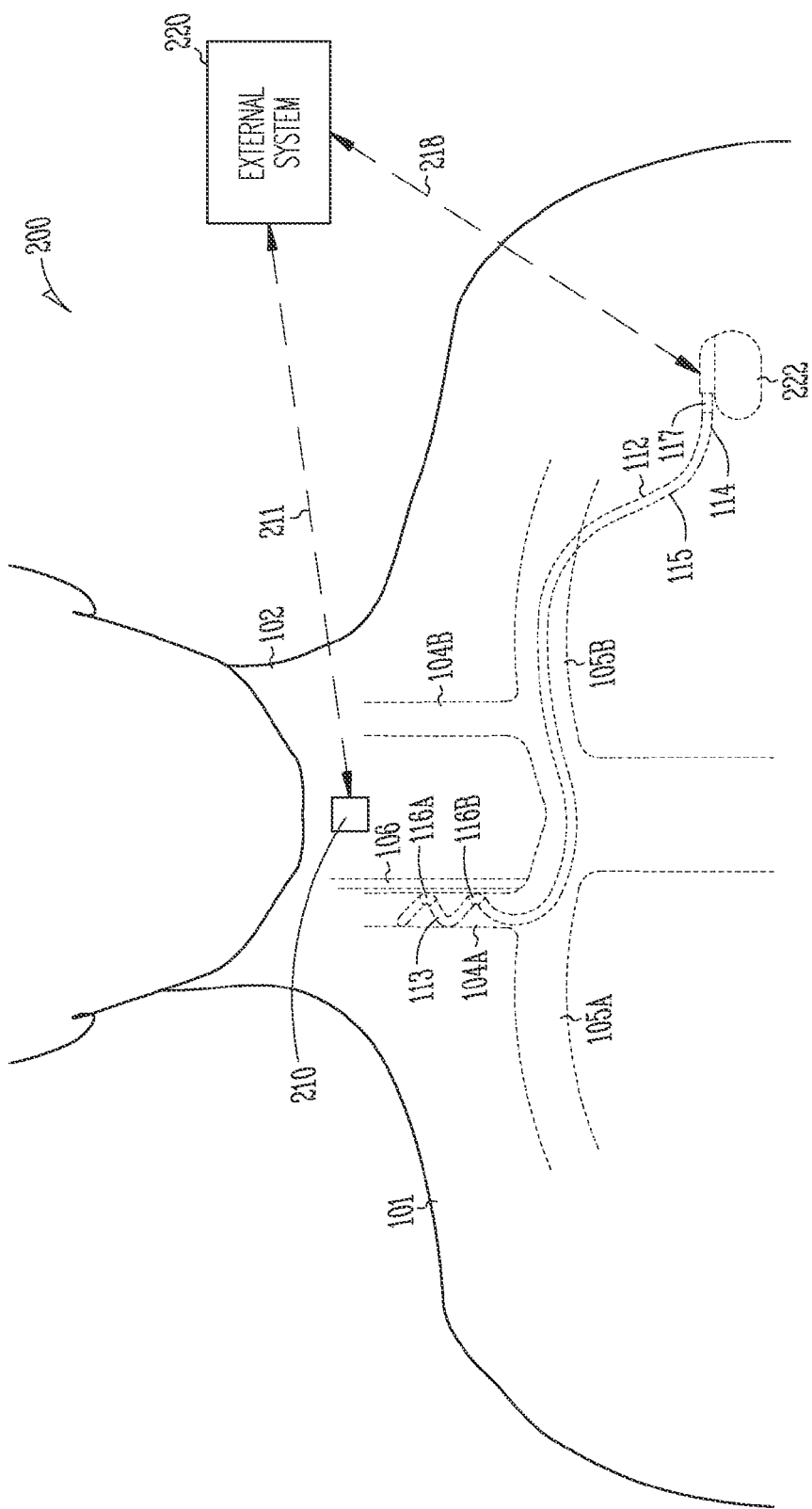
FIG. 2 is an illustration of another embodiment of the neural stimulation system and portions of the environment in which the neural stimulation system is used.

FIG. 2 is an illustration of an embodiment of a neural stimulation system 200 and portions of the environment in which system 200 is used. System 200 differs from system 100 primarily in that the neural stimulation is delivered from an implantable medical device 222 implanted in body 101. In one embodiment, FIGS. 1 and 2 illustrate different stages of implantation and use of an implantable neural stimulation system. FIG. 1 illustrates a system setup in the middle of an implantation procedure during which lead 112 is inserted with electrodes 116A-B placed to achieve desirable performance of vagal nerve stimulation. FIG. 2 illustrates the system set-up after the implantable neural stimulation system is fully implanted, such as during the end stage of the implantation procedure when the implantable neural stimulation system is programmed for chronic use or during a follow-up examination during which the implantable neural stimulation system is adjusted if necessary.

An activity sensor 210 represents an embodiment of activity sensor 110 that is capable of communicating with an external system 220 via a wireless link. In one embodiment, activity sensor 110 and external system 220 are electrically connected using a cable, and a communication link 211 represents the cable. In another embodiment, activity sensor 110 and external system 220 are wirelessly coupled through telemetry such as a radio-frequency electromagnetic telemetry link, and communication link 211 represents the telemetry link.

Implantable medical device 222 delivers the neural stimulation through one or both of electrodes 116A-B. After electrodes 116A-B are placed, proximal end 114 of lead 112 is connected to implantable medical device 222 via connector 117. In one embodiment, the housing of implantable medical device 222 functions as a reference electrode, and the neural stimulation can be delivered using any pair of electrodes selected from electrodes 116A-B and the housing of implantable medical device 222. In one embodiment, neural activity in vagus nerve 106 is sensed using any pair of electrodes selected from electrodes 116A-B and the housing of implantable medical device 222.

In one embodiment, in addition to the neural stimulation circuit, implantable medical device 222 includes other monitoring or therapeutic circuits or devices such as one or more of cardiac pacemaker, cardioverter/defibrillator, drug delivery device, and biological therapy device. External system 220 provides for control of and communication with implantable medical device 222 by the user. External system 220 and implantable medical device 222 are communicatively coupled via a telemetry link 218. In one embodiment, external system 220 includes a programmer. In another embodiment, external system 220 is a patient management system including an external device communicating with implantable medical device 222 via telemetry link 218, a remote device in a remote location, and a telecommunication network linking the external device and the remote device. The patient management system allows access to implantable medical device 222 from the remote location, for purposes such as monitoring patient status and adjusting therapies. In one embodiment, telemetry link 218 is an inductive telemetry link. In an alternative embodiment, telemetry link 218 is a far-field radio-frequency telemetry link.

Figure 3:
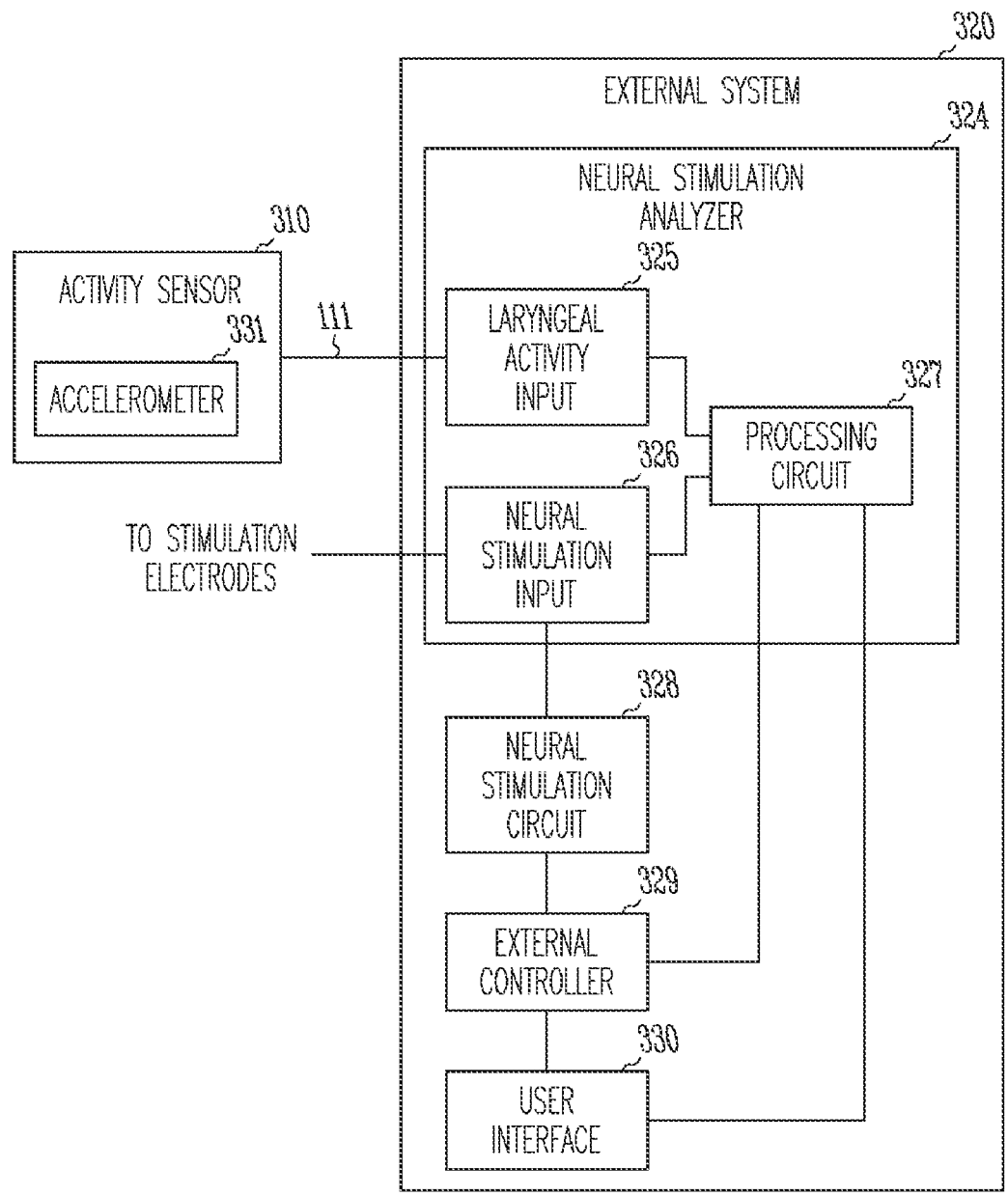
FIG. 3 is a block diagram illustrating an embodiment of portions of a circuit of the neural stimulation system of FIG. 1.

FIG. 3 is a block diagram illustrating an embodiment of portions of a circuit of system 100, including an activity sensor 310 coupled to an external system 320 by cable 111. Activity sensor 310 is an embodiment of activity sensor 110 and includes an accelerometer 331 to sense an acceleration signal being the signal indicative of laryngeal activity. Accelerometer 331 has characteristics suitable for sensing the magnitude and frequency of vibrations of the larynx that indicate activity in the vagus nerve when vagal nerve stimulation is delivered. In one embodiment, accelerometer 331 represents a plurality of accelerometers allowing for selection of an acceleration signal as the signal indicative of laryngeal activity based on the signal quality. External system 320 includes a neural stimulation analyzer 324, a neural stimulation circuit 328, an external controller 329, and a user interface 330. Neural stimulation analyzer 324 includes a laryngeal activity input 325, a neural stimulation input 326, and a processing circuit 327. Laryngeal activity input 325 receives the signal indicative of laryngeal activity from activity sensor 310 via cable 111. Neural stimulation input 326 receives a signal indicative of the delivery of the neural stimulation to the vagus nerve. Processing circuit 327 processes the signal indicative of laryngeal activity for analyzing the operation and performance of system 100 using that signal. Neural stimulation circuit 328 delivers the neural stimulation to stimulation electrodes such as electrodes 116A-B. External controller 329 controls overall operation of external system 320, including the delivery of the neural stimulation from neural stimulation circuit 328. User interface 330 allows the user to control the neural stimulation and monitor the response of the vagus nerve to the neural stimulation using the signal indicative of laryngeal activity.

Figure 4:
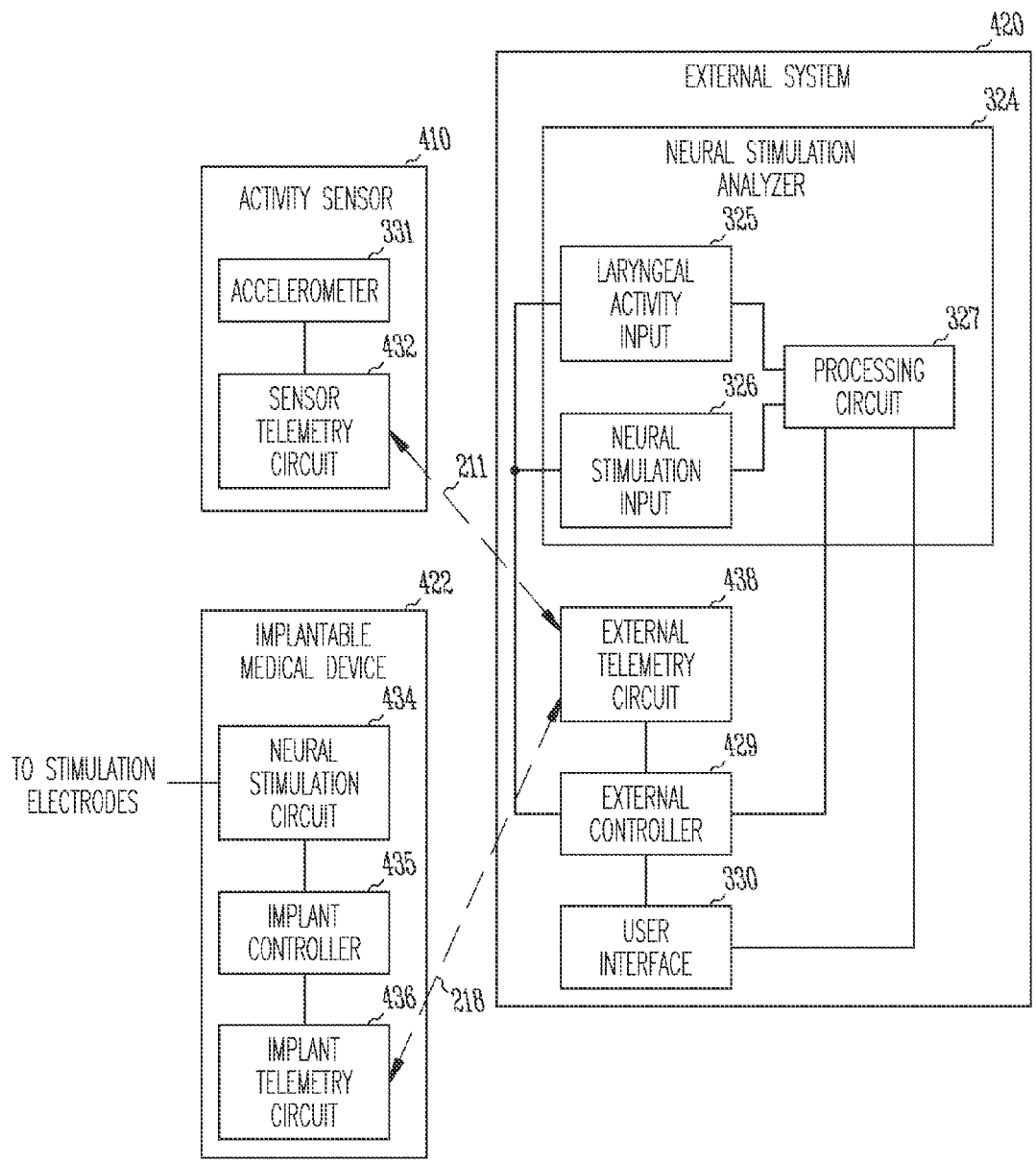
FIG. 4 is a block diagram illustrating an embodiment of portions of a circuit of the neural stimulation system of FIG. 2.

FIG. 4 is a block diagram illustrating an embodiment of portion of a circuit of system 200, including an activity sensor 410 coupled to an external system 420 via communication link 211 and an implantable medical device 422 coupled to external system 420 via telemetry link 218. Activity sensor 410 is an embodiment of activity 210 and includes accelerometer 331 and a sensor telemetry circuit 432. In the illustrated embodiment, communication link 211 is a telemetry link. Sensor telemetry circuit 432 transmits the sensed signal indicative of laryngeal activity to external system 420 via telemetry link 211. In another embodiment, communication link 211 is a cable providing an electrical connection between accelerometer 331 and laryngeal activity input 325. External system 420 includes neural stimulation analyzer 324, external telemetry circuit 438, external controller 429, and user interface 330. External telemetry circuit 438 receives the signal indicative of laryngeal activity from activity sensor 410 via communication link 211 and communicates with implantable medical device 422 via telemetry link 218 to control the neural stimulation delivered from implantable medical device 422. External controller 429 controls overall operation of external system 420, including the transmission of commands for controlling the neural stimulation delivered from the implantable medical device 422. Implantable medical device 422 includes a neural stimulation circuit 434, an implant controller 435, and an implant telemetry circuit 436. Neural stimulation circuit 434 delivers the neural stimulation through stimulation electrodes such as electrodes 116A-B. Implant controller 435 controls the delivery of the neural stimulation and is responsive to the commands transmitted from external system 420. Implant telemetry circuit 436 receives the commands from external system 420 via telemetry link 218 and when needed, transmits signals to external system 420 via telemetry link 218.

Figure 5:
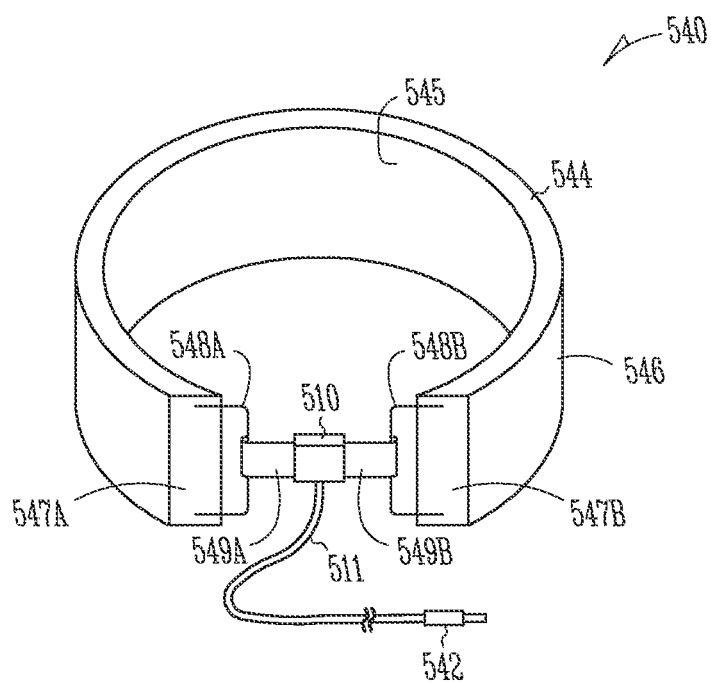
FIG. 5 is an illustration of an embodiment of a laryngeal activity sensor assembly of the neural stimulation system.

FIG. 5 is an illustration of an embodiment of a laryngeal activity sensor assembly 540 that allows for a substantially stable attachment of an activity sensor on a patient's neck over the larynx. Laryngeal activity sensor assembly 540 includes an activity sensor 510 and a neck-bracing structure configured to hold activity sensor 510 on the neck over the larynx. Activity sensor 510 senses the signal indicative of laryngeal activity and represents any of activity sensors 110, 210, 310, and 410. In the illustrated embodiment, a cable 511 is connected to activity sensor 510 and has a connector 542 to provide electrical connections between activity sensor 510 and external system 120 or 320. In a specific embodiment, cable 511 is detachably coupled to activity sensor 510. In another embodiment, activity sensor 510 is communicatively coupled to external system 220 or 420 via telemetry, and cable 511 is not needed.

Laryngeal activity sensor assembly 540 includes a neck brace 544 that is configured to wrap around a substantial portion of the neck and limits the movement of the neck. Neck brace 544 includes two ends 547A-B that are separated by a substantial gap over an anterior portion of the neck. In one embodiment, neck brace 544 is made of a material selected to limit the sensing of noise by activity sensor 510 by damping vibrations of environmental sources such as vibrations from equipment and activity of medical personnel. In one embodiment, neck brace 544 is made of a substantially soft material such as foam. Neck brace 544 has an interior surface 545 and an exterior surface 546. Interior surface 545 is configured for contacting the neck. In one embodiment, as illustrated in FIG. 5, neck brace 544 has a substantially even thickness between interior surface 545 and exterior surface 546. This thickness is, for example, between approximately 10 mm and 80 mm.

Laryngeal activity sensor assembly 540 further includes two brackets 548-B each affixed onto one of ends 547A-B. Straps 549A-B are coupled to brackets 548A-B and activity sensor 510. In one embodiment, straps 549A-B represent different portions of a single strap. In another embodiment, straps 549A-B represent two straps each coupled between activity sensor 510 and one of brackets 548A-B. Straps 549A-B are configured to press activity sensor 510 on the neck over the larynx for a substantially stable sensor placement. In one embodiment, straps 549A-B are stretchable elastic straps. In one embodiment, at least one of straps 549A-B is releasably coupled to one of brackets 547A-B. In one embodiment, straps 549A-B are coupled to the brackets in a way allowing adjustment of a position of activity sensor 510 in cranial/caudal directions.

In one embodiment, neck brace 544 is shaped to fit over the patient's head and/or shoulders to further limit the relative movement between activity sensor 510 and the larynx. In a specific embodiment, the edge of neck brace 544 that is toward the caudal direction when worn by a patient includes a contour that approximately fits over the patient's shoulders. This provides additional stability of sensor placement when the patient is sitting while the signal indicative of laryngeal activity is sensed.

Figure 6:
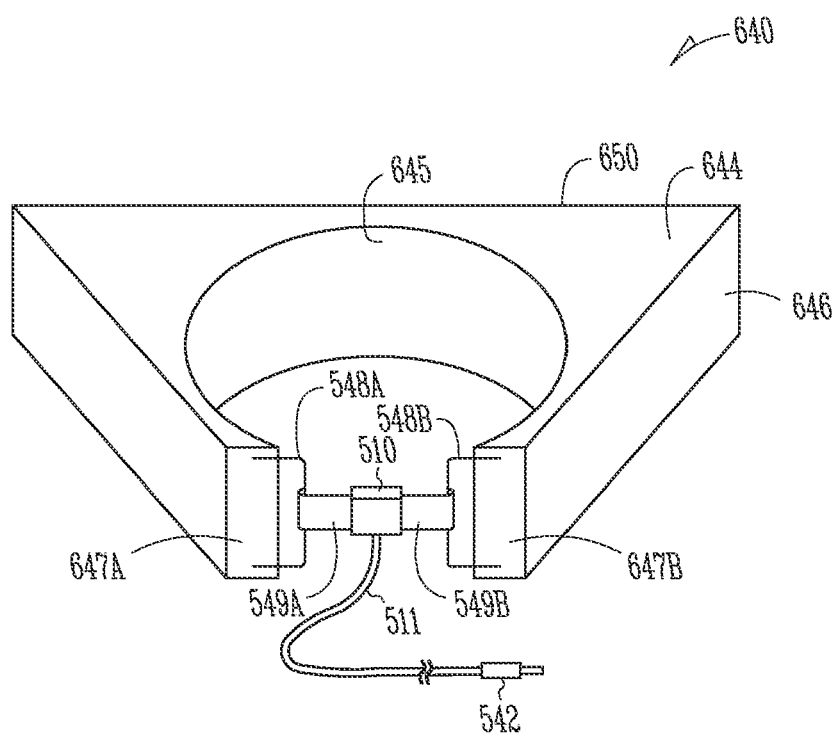
FIG. 6 is an illustration of another embodiment of the laryngeal activity sensor assembly of the neural stimulation system.

FIG. 6 is an illustration of an embodiment of a laryngeal activity sensor assembly 640, which is an alternative embodiment to laryngeal activity sensor assembly 540. Laryngeal activity sensor assembly 640 is similar to laryngeal activity sensor assembly 540 except for a neck brace 644, which is made of a material similar or identical to that of neck brace 544 but has a shape that is substantially different from that of neck brace 544.

Neck brace 644 includes two ends 647A-B that are separated by a substantial gap over an anterior portion of the neck. Brackets 548A-B are each affixed to one of ends 647A-B. Neck brace 644 has an interior surface 645 and an exterior surface 646. Interior surface 644 is configured for contacting the neck. Exterior surface 646 is configured to increase stability of the sensor placement by further limiting movement of the neck. In one embodiment, as illustrated in FIG. 6, exterior surface 646 has a flat back portion 650 over the posterior portion of the neck.

Figure 7:
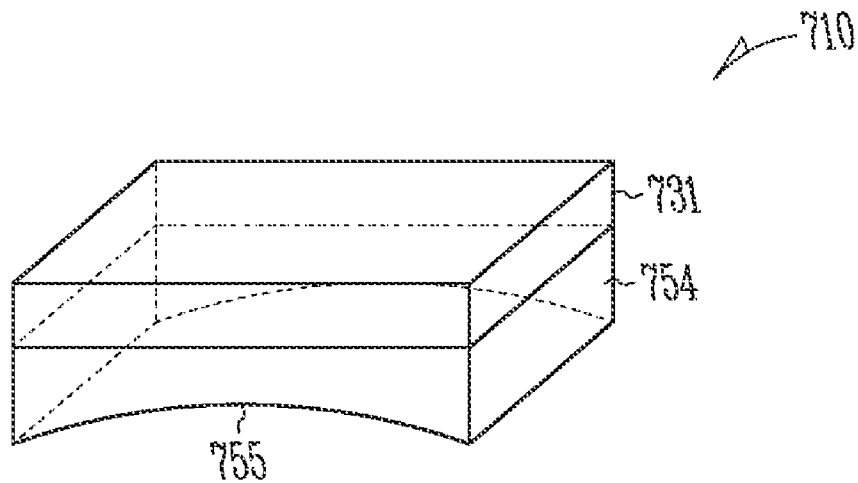
FIG. 7 is an illustration of an embodiment of an activity sensor including a sensor base.

FIG. 7 is an illustration of an embodiment of an activity sensor 710. Activity sensor 710 is an embodiment of activity sensor 510 that includes an accelerometer 731 affixed onto a sensor base 754. Accelerometer sensor 731 represents a specific embodiment of accelerometer 331 and senses the signal indicative of laryngeal activity. Sensor base 754 is configured to be an interface between accelerometer sensor 731 and the neck, and has a surface 755 curved to fit onto the neck.

Figure 8:
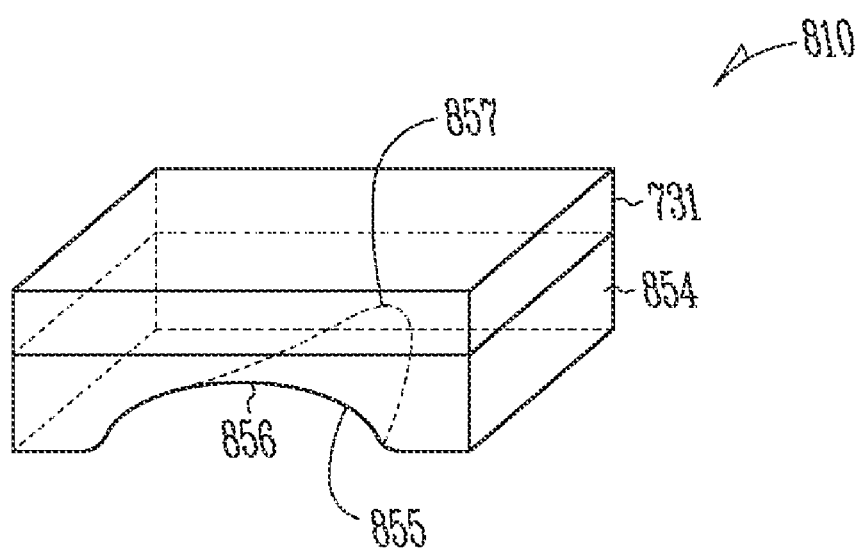
FIG. 8 is an illustration of another embodiment of the activity sensor including the sensor base.

FIG. 8 is an illustration of an embodiment of an activity sensor 810. Activity sensor 810 is an embodiment of activity sensor 710 and includes accelerometer 731 and a sensor base 854. Sensor base 854 has a surface 855 curved to fit onto the neck of a male patient over part of his thyroid cartilage. In one embodiment, as illustrated in FIG. 8, surface 855 includes a recess 856 on one end and a notch 857 at the other end for fitting over part of the thyroid cartilage.

Figure 9:
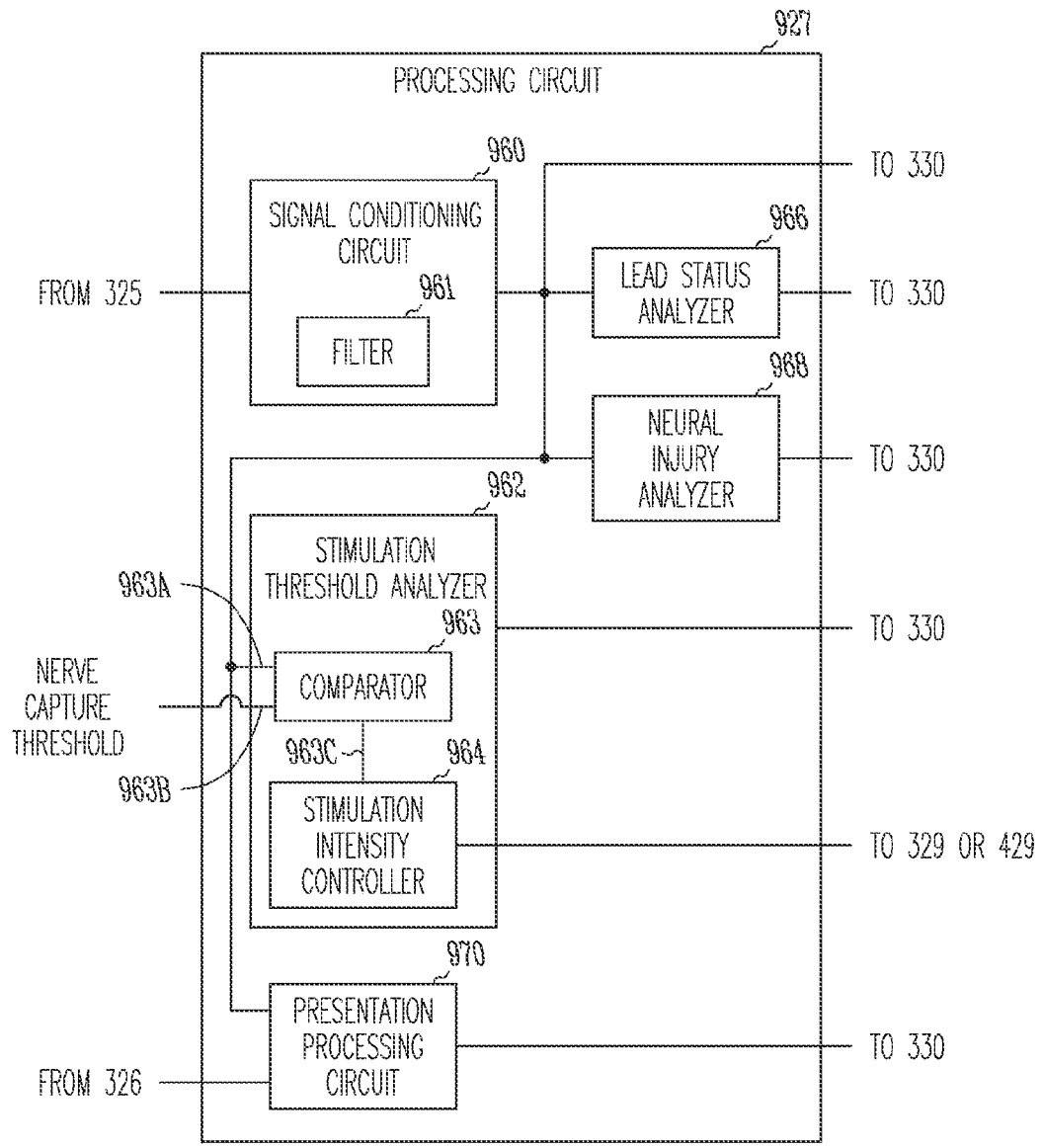
FIG. 9 is a block diagram illustrating an embodiment of a processing circuit of a neural stimulation analyzer of the neural stimulation system.

FIG. 9 is a block diagram illustrating an embodiment of a processing circuit 927, which is a specific embodiment of processing circuit 327. Processing circuit 927 includes a signal conditioning circuit 960, a stimulation threshold analyzer 962, a lead status analyzer 966, a neural injury analyzer 968, and a presentation processing circuit 970.

Signal conditioning circuit 960 conditions the signal indicative of laryngeal activity for analysis or presentation purposes. Signal conditioning circuit 960 increases the signal-to-noise ratio of the signal indicative of laryngeal activity, where the signal includes components of the signal indicative of laryngeal activity that result from the vagal nerve stimulation, and the noise includes components of the signal indicative of laryngeal activity that is not an effect of the vagal nerve stimulation. Signal conditioning circuit 960 includes a filter 961 that filters out the noise. In one embodiment, filter 961 has a pass-band selected based on the frequency at which neural stimulation pulses are delivered to the vagus nerve.

Stimulation threshold analyzer 962 automatically measures a stimulation threshold associated with each pair of stimulation electrodes via which the neural stimulation is delivered to the vagus nerve, such as stimulation electrodes 116A-B. The stimulation threshold is the minimum stimulation intensity at which the neural stimulation activates the vagus nerve. Stimulation threshold analyzer 962 includes a comparator 963 and a stimulation intensity controller 964. Comparator 963 includes a first input 963A to receive an amplitude of the signal indicative of laryngeal activity, a second input 963B to receive a nerve capture threshold, and an output 963C that indicates a nerve capture when the amplitude of the signal indicative of laryngeal activity exceeds the nerve capture threshold. That is, an amplitude of the signal indicative of laryngeal activity that exceeds the nerve capture threshold is the indication that the neural stimulation has elicited action potentials propagating in the vagus nerve. In various embodiments, the nerve capture threshold is determined empirically based a patient population or each individual patient. Stimulation intensity controller 964 adjusts the stimulation intensity of the neural stimulation such that a plurality of stimulation intensities may be tested, and stimulation threshold analyzer 962 automatically determines the stimulation threshold by selecting the tested minimum stimulation intensity that results in a nerve capture. In various embodiments in which the neural stimulation includes delivery of electrical pulses, the stimulation intensity is controlled by stimulation amplitude (voltage or current) and/or stimulation pulse width. Stimulation intensity controller 964 adjusts the stimulation intensity by adjusting the stimulation amplitude, the stimulation pulse width, or both. In one embodiment, stimulation intensity controller 964 increases the stimulation intensity from an initial intensity until the nerve capture is indicated or a specified maximum stimulation intensity is reached. If the maximum stimulation intensity is reached before the nerve capture is indicated, the stimulation electrodes are repositioned before the determination of the stimulation threshold continues. In one embodiment, stimulation threshold analyzer 962 presents the minimum capture intensity at which the nerve capture is indicated when the stimulation intensity is being increased as the stimulation threshold. In another embodiment, after the minimum capture intensity is reached, stimulation intensity controller 964 decreases the stimulation intensity from that minimum capture intensity until the nerve capture is no longer indicated. Stimulation threshold analyzer 962 presents the minimum stimulation intensity at which the nerve capture is indicated when the stimulation intensity is being decreased as the stimulation threshold.

Lead status analyzer 966 detects dislodgment or breakage of a lead for delivering the neural stimulation, such as lead 112, by detecting a substantial change in the stimulation threshold between two stimulation threshold measurements. In one embodiment, upon detection of the dislodgment or breakage of the lead, lead status analyzer 966 produces a warning signal or message to be presented to the user through user interface 330.

Neural injury analyzer 968 detects a nerve injury by monitoring the change in the stimulation threshold and/or the change in the amplitude of the signal indicative of laryngeal activity over time. The laryngeal nerves include efferent nerve fibers. A neural injury occurring in the nervous path between the stimulation site and the larynx is indicated by absence or weakening of laryngeal response to the vagal nerve stimulation. A weakened laryngeal response may serve as an early indication of the neural injury. Appropriate treatments may be applied in response, thereby preventing the neural injury from progressing to a degree associated with a major functional impairment. In one embodiment, neural injury analyzer 968 monitors the change in the stimulation threshold over time, determines the speed of the change in the stimulation threshold, and detects a neural injury based on the speed of the change in the stimulation threshold. In another embodiment, neural injury analyzer 968 monitors the amplitude of the signal indicative of laryngeal activity in response to delivering the neural stimulation at a specified stimulation intensity over time, determines the speed of the change in the amplitude of the signal indicative of laryngeal activity, and detects a neural injury based on the speed of the change in the amplitude of the signal indicative of laryngeal activity. In another embodiment, neural injury analyzer 968 detects a substantial change in neural conduction velocity as an indication of neural injury. In a specific embodiment, neural injury analyzer 968 measures the neural conduction velocity as the ratio of a neural conduction time to an estimated neural conduction distance, and detects a neural injury based on the change in the neural conduction velocity over time. The neural conduction time is the time interval between the delivery of a stimulus and the beginning of the elicited response in the signal indicative of laryngeal activity. In another specific embodiment, neural injury analyzer 968 measures the neural conduction time being the time interval between the delivery of a stimulus and the beginning of the elicited response in the signal indicative of laryngeal activity, and detects a neural injury based on the change in the neural conduction time over time. In one embodiment, upon detection of a possible neural injury, neural injury analyzer 968 produces a warning signal or message to be presented to the user through user interface 330.

Presentation processing circuit 970 processes the signal indicative of laryngeal activity for presentation to the user in one or more forms through user interface 330. In one embodiment, presentation processing circuit 970 also processes other signals, messages, and/or indicators related to laryngeal activity, lead status, neural injury, and/or other related information for presentation to the user through user interface 330.

Figure 10:
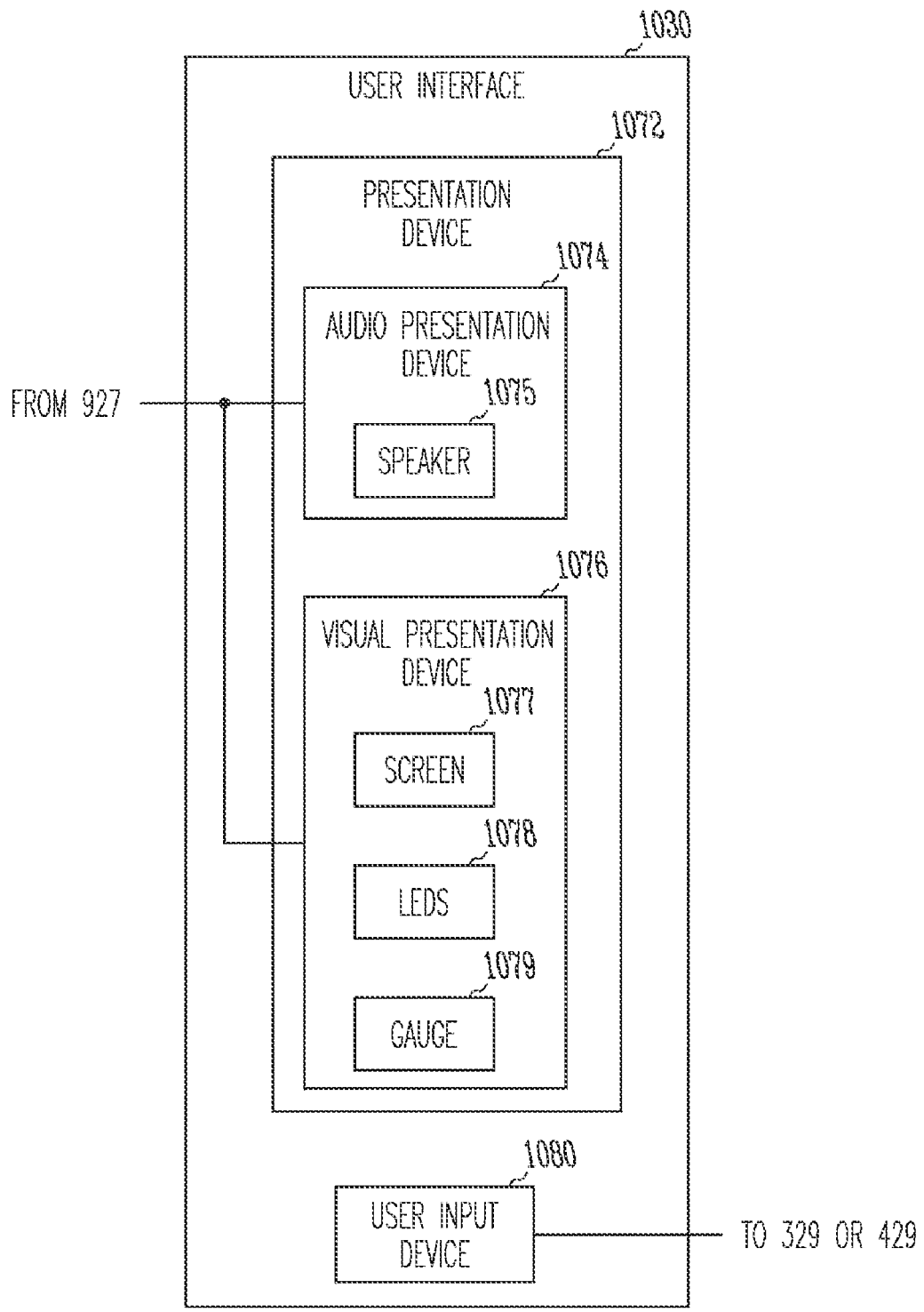
FIG. 10 is a block diagram illustrating an embodiment of a user interface of the neural stimulation system.

FIG. 10 is a block diagram illustrating an embodiment of a user interface 1030. User interface 1030 is a specific embodiment of user interface 330 and includes a presentation device 1072 and a user input device 1080. Presentation device 1072 presents indicators of the laryngeal activity and the neural stimulation in one or more forms. User input device 1080 allows the user to control the neural stimulation by entering commands and parameters, and to control presentation device 1080 by choosing how the laryngeal activity and the neural stimulation are indicated.

In the illustrated embodiment, presentation device 1072 includes an audio presentation device 1074 and a visual presentation device 1076. Audio presentation device 1074 includes a speaker 1075 that generates an audible tone indicative of the laryngeal activity. The audible tone has a pitch indicative a frequency at which the larynx vibrates and/or a magnitude of the laryngeal activity. In one embodiment, the audible tone has a pitch indicative the frequency at which the larynx vibrates and a volume indicative of the magnitude of the laryngeal activity. When the neural stimulation is delivered as electrical pulses, as the stimulation frequency (the frequency at which the electrical pulses are delivered) increases, the muscular response in the larynx may change from a twitch response to a tentatic response (which means the muscle stays contracted during the delivery of an entire pulse train). In one embodiment, the stimulation frequency is selected such that the delivery of the electrical pulses elicits a twitch response but not a tentatic response. Thus, the frequency at which the larynx vibrates is the stimulation frequency, and the magnitude of the laryngeal activity is a function of the stimulation intensity.

Visual presentation device 1076 includes a screen 1077, light-emitting diodes (LEDs) 1078, and a gauge 1079. Screen 1077 displays the signal indicative of laryngeal activity and a signal indicative of the neural stimulation. Examples of the signal indicative of the neural stimulation include neural stimulation markers and a neural signal indicative of vagal nerve activity sensed by the stimulation electrodes such as electrodes 116A-B. In various embodiments, screen 1077 further displays one or more sensed physiological signals such as electrocardiogram (ECG) and various signals, messages, and/or indicators related to laryngeal activity, lead status, neural injury, and/or other related information. LEDs 1078 are each turned on when the amplitude of the signal indicative of laryngeal activity exceeds a predetermined threshold. A plurality of different thresholds each associated with one or more of LEDs 1078 allows for selective lighting of each of LEDs 1078 according to the amplitude of the signal indicative of laryngeal activity. Gauge 1079 indicates the magnitude of the laryngeal activity. In one embodiment, gauge 1079 is in the form of an image displayed in screen 1077. In another embodiment, gauge 1079 is a device separated from screen 1077.

Figure 11:
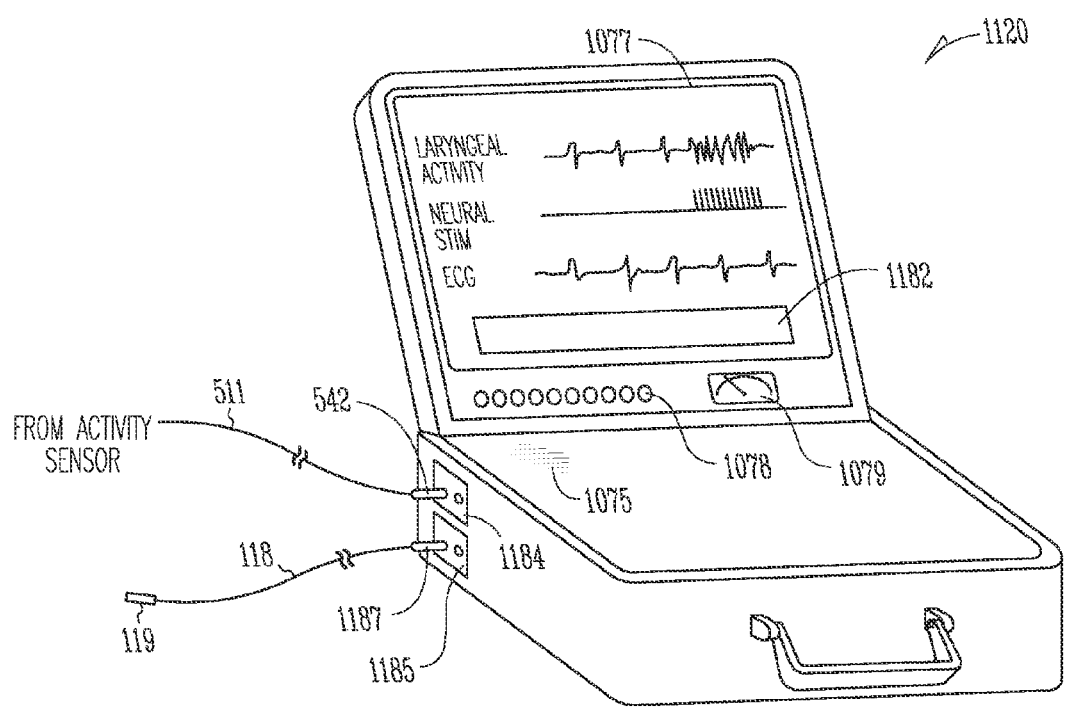
FIG. 11 is an illustration of an embodiment of an external programmer of the neural stimulation system.

FIG. 11 is an illustration of an external programmer 1120, which is an embodiment of external system 120, 220, 320, or 420. In the illustrated embodiment, external programmer 1120 includes speaker 1075, screen 1077, LEDs 1078, and gauge 1079. In other embodiments, external programmer 1120 includes any one or more of speaker 1075, screen 1077, LEDs 1078, and gauge 1079. In the illustrated embodiment, screen 1077 includes a trace of the signal indicative of laryngeal activity, a signal indicative of the neural stimulation, a trace and an ECG signal, and an area 1182 displaying the various signals, messages, and/or indicators related to laryngeal activity, lead status, neural injury, and/or other related information.

Programmer 1120 receives the signal indicative of laryngeal activity and controls the neural stimulation by allowing the user to enter commands and parameters. In the illustrated embodiment, programmer 1120 includes a sensor input 1184 and a stimulation output 1185. Activity sensor 510 senses the signal indicative of laryngeal activity and transmits the sensed signal to programmer 1120 through cable 511 and connector 542, which is detachably connected to sensor input 1184. Cable 118 with a connector 1187 detachably connected to stimulation output 1185 and connector 119 provides for connection to stimulation electrodes such as stimulation electrodes 116A-B on lead 112. This allows for delivery of the neural stimulation from a neural stimulation circuit of programmer 1120. In one embodiment, programmer 1120 is also capable of receiving the signal indicative of laryngeal activity from activity sensor 510 via telemetry. In one embodiment, programmer 1120 is also capable of controlling the delivery of the neural stimulation from a neural stimulation circuit of an implantable medical device via telemetry.

Figure 12:
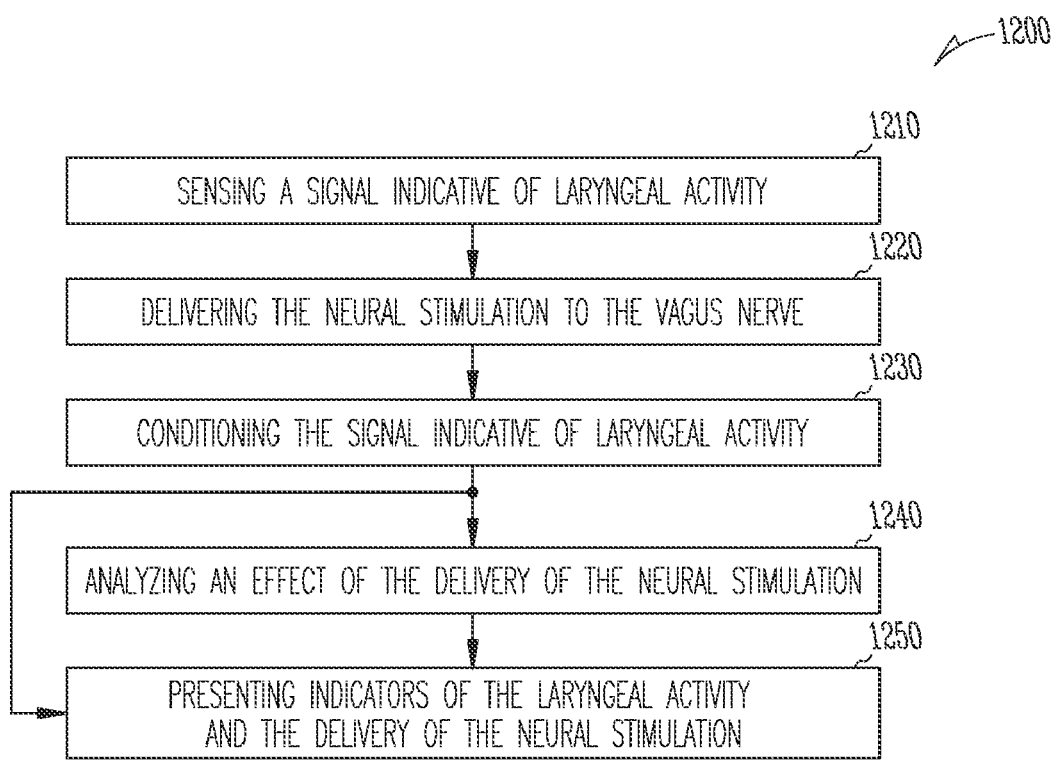
FIG. 12 is a flow chart illustrating an embodiment of a method for analyzing effect of vagal nerve stimulation using a signal indicative of laryngeal activity.

FIG. 12 is a flow chart illustrating an embodiment of a method 1200 for analyzing effect of neural stimulation using a signal indicative of laryngeal activity. In one embodiment, method 1200 is performed by systems 100 or 200.

The signal indicative of laryngeal activity is sensed at 1210. The neural stimulation is delivered to the vagus nerve at 1220. The signal indicative of laryngeal activity is conditioned at 1230, to isolate laryngeal activity resulting from the delivery of the neural stimulation from other components of the sensed signal indicative of laryngeal activity. An effect of the delivery of the neural stimulation is analyzed at 1240 using the signal indicative of laryngeal activity. Indicators of the laryngeal activity and the delivery of the neural stimulation are presented at 1250. In one embodiment, an audible tone indicative of the laryngeal activity is generated. In a specific embodiment, the audible tone has a pitch indicative a magnitude of the laryngeal activity. In another specific embodiment, the audible tone has a pitch indicative a frequency at which the larynx vibrates and a volume indicative of a magnitude of the laryngeal activity. In another embodiment, a visual indication of the laryngeal activity is produced. Examples of the visual indication include traces of the signal indicative of laryngeal activity, a signal indicative of the neural stimulation, and a gauge indicative of magnitude of the laryngeal activity.

Figure 13:
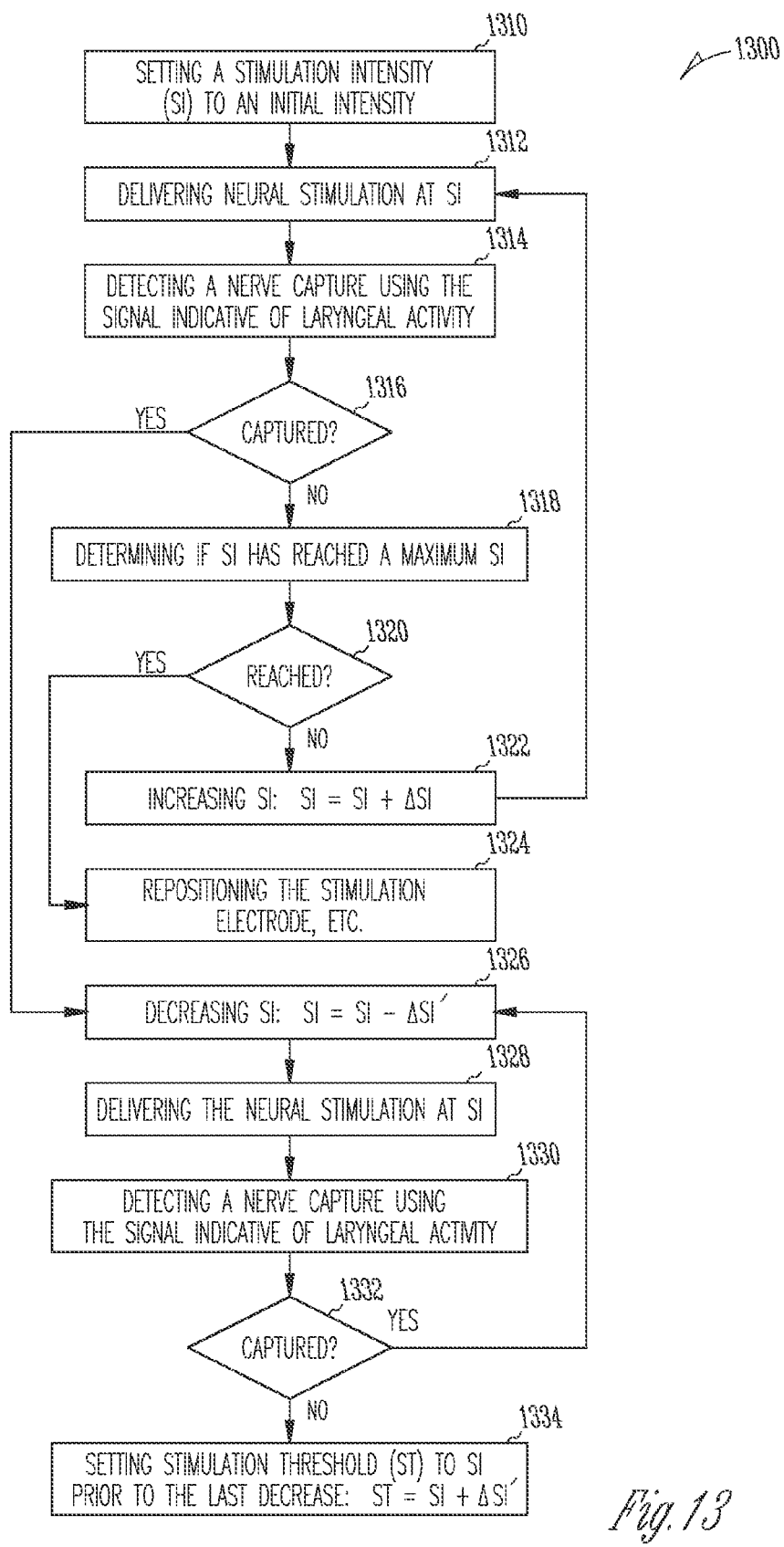
FIG. 13 is a flow chart illustrating an embodiment of a method for automatically determining a stimulation threshold for the vagal nerve stimulation using the signal indicative of laryngeal activity.

FIG. 13 is a flow chart illustrating an embodiment of a method 1300 for automatically determining a stimulation threshold for the neural stimulation using the signal indicative of laryngeal activity. The stimulation threshold is indicative of the minimum stimulation intensity required to capture the vagus nerve. In one embodiment, method 1300 is performed by stimulation threshold analyzer 962.

The stimulation intensity (SI) of the neural stimulation is set to an initial intensity at 1310. In one embodiment, the initial intensity is an empirically determined parameter. In one embodiment, the initial intensity is selected by the user. When the neural stimulation is delivered as electrical pulses, the SI is controlled by the (voltage or current) and the pulse width of each of the electrical pulses.

The neural stimulation is delivered to the vagus nerve at the SI at 1312. A nerve capture is being detected using the signal indicative of laryngeal activity at 1314, by comparing the amplitude of the signal indicative of laryngeal activity to a nerve capture threshold. The nerve capture is detected at 1316 if the amplitude of the signal indicative of laryngeal activity exceeds the nerve capture threshold.

If the nerve capture is not detected at 1316, whether the SI has reached a specified maximum SI is determined at 1318. If the SI has reached the specified maximum SI at 1320, the stimulation electrodes are repositioned, or other approaches must be taken to increase the specified maximum SI and/or decrease the stimulation threshold, at 1324. In one embodiment, the stimulation electrodes are "repositioned", or selected, electronically. The neural stimulation is delivered to the vagus nerve using an active set of stimulation electrodes electronically selected from multiple available sets of stimulation electrodes, and electronically repositioning means electronically selecting a different set of available stimulation electrodes to be the active set of stimulation electrodes. If the SI has not reached the specified maximum SI at 1320, the SI is increased by $\Delta SI$ at 1322, and method 1300 returns to 1312 to continue therefrom. In one embodiment, the stimulation threshold is determined as a voltage of an electrical pulse at a specified pulse width. In a specific embodiment, $\Delta SI$ is about 0.2 V.

If the nerve capture is detected at 1316, the current SI is the minimum capture intensity at which the nerve capture is detected as the stimulation intensity is being increased. The SI is decreased from that minimum capture intensity, with $\Delta SI'$ being the decrement step, at 1326. In one embodiment, $\Delta SI'$ and $\Delta SI$ are set to the same value. In a specific embodiment, $\Delta SI'$ is about 0.2 V.

The neural stimulation is delivered at the (decreased) SI at 1328. A nerve capture is being detected using the signal indicative of laryngeal activity at 1330, by comparing the amplitude of the signal indicative of laryngeal activity to the nerve capture threshold. The nerve capture is detected at 1332 if the amplitude of the signal indicative of laryngeal activity exceeds the nerve capture threshold.

If the nerve capture is detected at 1332, method 1300 returns to 1326 to further decrease the SI and continue therefrom. If the nerve capture is not detected at 1332, the SI prior to the last decrease at 1326 is set to the stimulation threshold at 1334. That is, the stimulation threshold (ST) is the current SI (after 1326) plus $\Delta SI'$.

Figure 14:
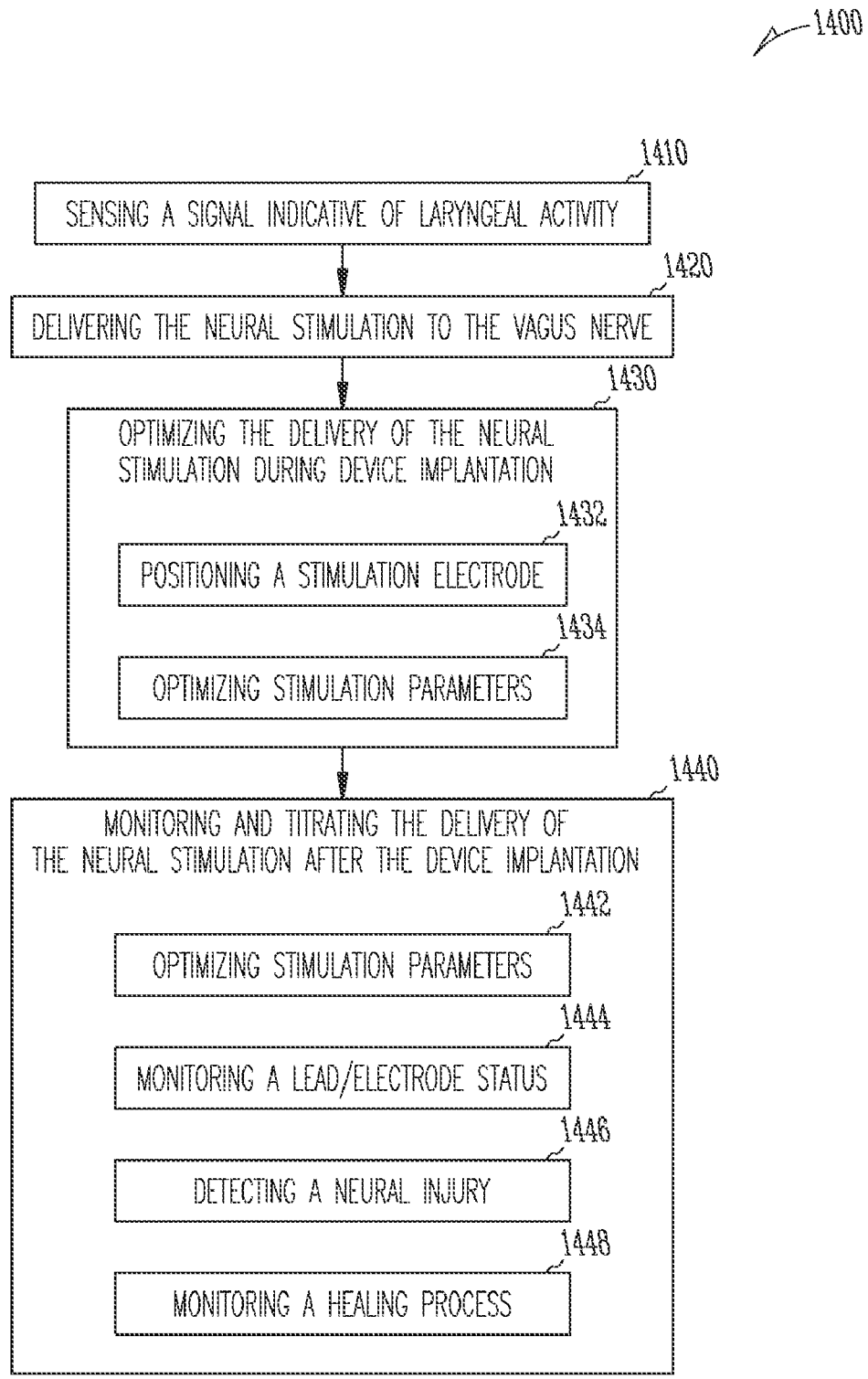
FIG. 14 is a flow chart illustrating an embodiment of a method for monitoring and titrating the vagal nerve stimulation acutely and chronically using the signal indicative of laryngeal activity.

FIG. 14 is a flow chart illustrating an embodiment of a method 1400 for monitoring and titrating the neural stimulation acutely and chronically using the signal indicative of laryngeal activity. Method 1400 is performed during and after the implantation of an implantable neural stimulation system. In one embodiment, method 1400 is performed with systems 100 and/or 200.

The signal indicative of laryngeal activity is sensed at 1410. The neural stimulation is delivered to the vagus nerve at 1420. The laryngeal activity indicates the response of the vagus nerve to the neural stimulation. The response depends on, for example, the position of the stimulation electrodes, stimulation parameters, condition of the neural stimulation system such as condition of the leads and/or stimulation electrodes, existence and progress of neural injury, and healing of tissue surrounding the stimulation electrodes following implantation of the stimulation electrodes.

The delivery of the neural stimulation is optimized during the implantation of an implantable medical device at 1430. This includes, for example, positioning a stimulation electrode at 1432 and optimizing stimulation parameters associated with that stimulation electrode at 1434. In various embodiments, 1432 and 1434 are performed for each stimulation electrode or each pair of stimulation electrodes. The stimulation electrode is placed for delivering the neural stimulation to the vagus nerve using the signal indicative of laryngeal activity. In one embodiment, the stimulation electrode is incorporated onto the distal end of a transvenous lead. The transvenous lead is inserted into the vascular system such that the stimulation electrode is in a position within an approximate target region in an internal jugular vein. A stimulation threshold is determined automatically, such as by performing method 1300, for that position using the signal indicative of laryngeal activity. If the stimulation threshold is not satisfactory, the stimulation electrode is placed in another position within the approximate target region, and the stimulation threshold is determined for the new position. The repositioning and threshold determination are repeated until a satisfactory stimulation threshold is obtained. In one embodiment, the repositioning is performed electronically. The neural stimulation is delivered using an active stimulation electrode electronically selected from a plurality of available stimulation electrodes, and placing a stimulation electrode in another position means electronically selecting an available stimulation electrode placed in another position to be the active stimulation electrode. In another embodiment, after the transvenous lead is inserted and the stimulation electrode is in the position within the approximate target region, a minimal electrical current is delivered to the vagus nerve using the stimulation electrode. The amplitude is kept low but sufficient to produce laryngeal activity that can be sensed. The amplitude of the signal indicative of laryngeal activity is monitored while the stimulation electrode is moved to evaluate positions within the approximate target region. The stimulation electrode is positioned permanently in the location associated with a maximum amplitude of the signal indicative of laryngeal activity.

After the stimulation electrode is positioned at 1432, the stimulation parameters associated with the stimulation electrode are optimized at 1434. In one embodiment, this includes determining the stimulation threshold associated with the stimulation electrode automatically, such as by performing method 1300, for the permanent position of the stimulation electrode. The stimulation intensity associated with the stimulation electrode is programmed for chronic use based on the stimulation threshold, such as by setting the stimulation intensity to a value exceeding the stimulation threshold by a predetermined margin.

The delivery of the neural stimulation is monitored and titrated after the device implantation at 1440. This includes, for example, optimizing stimulation parameters at 1442, monitoring a lead or stimulation electrode status at 1444, detecting a neural injury at 1446, and monitoring a healing process at 1448. In various embodiments, 1440, or any portion thereof, is performed by the user during a follow-up examination according a specified schedule, such as on an approximately periodic basis.

The stimulation parameters are optimized at 1442. In one embodiment, this includes determining the stimulation threshold associated with each stimulation electrode automatically, such as by performing method 1300. If the stimulation threshold associated with an electrode has changed substantially from the previous measurement, the stimulation intensity associated with that stimulation electrode is adjusted based on the new stimulation threshold, such as by setting the stimulation intensity to a value exceeding the new stimulation threshold by a predetermined margin.

The lead or stimulation electrode status is monitored at 1444. This includes, for example, detection of possible displacement, dislodgement, and breakage of the lead. A possible lead problem is indicated by a substantial, abnormal change in the stimulation threshold between measurements of the stimulation threshold.

A neural injury is detected at 1446. In one embodiment, the neural injury is detected by monitoring the change in the stimulation threshold over time. A possible neural injury is indicated by a detected abnormal speed of change in the stimulation threshold. In another embodiment, the neural injury is detected by monitoring the amplitude of the signal indicative of laryngeal activity in response to delivering neural stimulation at a specified stimulation intensity over time. A possible neural injury is indicated by a detected abnormal speed of the change in the amplitude of the signal indicative of laryngeal activity. The neural injury detection at 1446 allows for early discovery of a neural injury that needs immediate treatment to prevent from developing into a major functional impairment.

A healing process is monitored at 1448. After the implantation of the implantable medical device and the lead or stimulation electrodes, it may take weeks or months for the tissue injured during the implantation to heal and the interface between the body and the implanted system to stabilize. This healing process is monitored by monitoring the change in the stimulation threshold over time. A stabilized stimulation threshold is an indication that the healing process may have substantially completed.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A neural stimulation system for applying neural stimulation through a lead to a body having a neck, a larynx, and a vagus nerve, the system comprising:
   an activity sensor configured to sense a signal indicative of laryngeal activity;
   a neural stimulation circuit configured to deliver neural stimulation pulses to the vagus nerve; and
   a neural stimulation analyzer communicatively coupled to the activity sensor and the neural stimulation circuit, the neural stimulation analyzer including a stimulation threshold analyzer configured to measure a stimulation threshold using the signal indicative of laryngeal activity, the stimulation threshold being a minimum stimulation intensity required for the neural stimulation pulses to elicit a neural response in the vagus nerve.

2. The system of claim 1, wherein the stimulation threshold analyzer comprises a comparator configured to indicate a nerve capture when the amplitude of the signal indicative of laryngeal activity exceeds the nerve capture threshold.

3. The system of claim 2, wherein the stimulation threshold analyzer comprises a stimulation intensity controller configured to increase a stimulation intensity from an initial intensity until the nerve capture is indicated or a predetermined maximum stimulation intensity is reached.

4. The system of claim 3, wherein the stimulation intensity controller is further configured to decrease the stimulation intensity, after the nerve capture is indicated, until the nerve capture is no longer indicated.

5. The system of claim 1, wherein the neural stimulation analyzer further comprises a lead status analyzer configured to detect dislodgement or breakage of the lead by detecting a change in the measured stimulation threshold between measurements.

6. The system of claim 1, wherein the neural stimulation analyzer further comprises a neural injury analyzer configured to detect a nerve injury by monitoring for a change in the measured stimulation threshold over time.

7. The system of claim 1, further comprising a presentation device configured to present indicators of the laryngeal activity and the delivery of the neural stimulation pulses.

8. The system of claim 7, wherein the presentation device comprises a speaker configured to generate an audible tone indicative of one or more of a frequency and a magnitude of the laryngeal activity.

9. The system of claim 7, comprising a laryngeal activity sensor assembly including the activity sensor and a neck-bracing structure configured to hold the activity sensor on the neck over the larynx.

10. The system of claim 9, wherein the activity sensor comprises an accelerometer.

11. A method for applying neural stimulation through a lead to a body having a neck, a larynx, and a vagus nerve, the method comprising:
   sensing a signal indicative of laryngeal activity;
   delivering neural stimulation pulses through the lead to the vagus nerve; and
   determining a stimulation threshold using the signal indicative of laryngeal activity, the stimulation threshold being a minimum stimulation intensity required for the neural stimulation pulses to elicit a neural response in the vagus nerve, the determining performed automatically by a processing circuit.

12. The method of claim 11, wherein determining the stimulation threshold comprises:
   setting a stimulation intensity of the neural stimulation to an initial intensity;
   detecting a nerve capture by comparing an amplitude of the signal indicative of laryngeal activity to a nerve capture threshold; and
   increasing the stimulation intensity from the initial intensity until the nerve capture is detected or a predetermined maximum stimulation intensity is reached.

13. The method of claim 12, wherein determining the stimulation threshold further comprises decreasing the stimulation intensity, after the nerve capture is detected, until the nerve capture is no longer detected.

14. The method of claim 11, further comprising detecting a lead dislodgement or breakage indicated by a substantial, abnormal change in the stimulation threshold.

15. The method of claim 11, further comprising detecting a neural injury by monitoring for a change in the stimulation threshold over time.

16. The method of claim 11, further comprising presenting indicators of the laryngeal activity.

17. The method of claim 16, wherein presenting the indicators of the laryngeal activity comprises producing an audible tone indicative of frequency and magnitude of the laryngeal activity.

18. The method of claim 16, wherein presenting the indicators of the laryngeal activity comprises turning on one or more light-emitting diodes when an amplitude of the signal indicative of laryngeal activity exceeds a predetermined threshold.

19. The method of claim 11, wherein sensing the signal indicative of laryngeal activity comprises placing an activity sensor on the neck over the larynx, the activity sensor configured to sense the signal indicative of laryngeal activity.

20. The method of claim 19, wherein sensing the signal indicative of laryngeal activity further comprises holding the activity sensor on the neck over the larynx using a neck brace coupled to the activity sensor and configured to wrap around a portion of the neck.

* * * * *